United States Patent
Brown et al.

(10) Patent No.: US 9,646,814 B2
(45) Date of Patent: May 9, 2017

(54) METHOD AND APPARATUS FOR REACTING IONS

(71) Applicant: Micromass UK Limited, Wilmslow (GB)

(72) Inventors: Jeffery Mark Brown, Hyde (GB); Kevin Giles, Stockport (GB); Steven Derek Pringle, Hoddlesden (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 14/895,323

(22) PCT Filed: Jun. 9, 2014

(86) PCT No.: PCT/GB2014/051768
§ 371 (c)(1),
(2) Date: Dec. 2, 2015

(87) PCT Pub. No.: WO2014/195735
PCT Pub. Date: Dec. 11, 2014

(65) Prior Publication Data
US 2016/0126077 A1    May 5, 2016

(30) Foreign Application Priority Data

Jun. 7, 2013   (EP) ..................................... 13170997
Jun. 7, 2013   (GB) .................................. 1310133.2

(51) Int. Cl.
*H01J 49/00*   (2006.01)
*G01N 27/62*   (2006.01)
*H01J 49/06*   (2006.01)

(52) U.S. Cl.
CPC ........ *H01J 49/0072* (2013.01); *G01N 27/622* (2013.01); *H01J 49/0031* (2013.01); *H01J 49/06* (2013.01); *H01J 49/062* (2013.01)

(58) Field of Classification Search
None
See application file for complete search history.

(56) References Cited

U.S. PATENT DOCUMENTS 7,759,638 B2 *   7/2010   Makarov ............... H01J 49/004
                                                                        250/281
7,851,751 B2 *   12/2010  Bateman ............. H01J 49/0031
                                                                        250/281

(Continued)

*Primary Examiner* — Jack Berman
(74) *Attorney, Agent, or Firm* — Diederiks & Whitelaw, PLC

(57) ABSTRACT

A method of mass spectrometry is disclosed having a mode comprising: providing a source of precursor ions and reagent ions for reacting with said precursor ions; providing a reaction region downstream of said source; providing an ion mobility separator between said source and said reaction region; providing a bypass cell between said source and said reaction region for guiding ions from said source to said reaction region without the ions passing through said ion mobility separator; guiding said precursor ions from said source, through said ion mobility separator so that said precursor ions separate according to their ion mobility and into said reaction region; and guiding said reagent ions from said source, through said bypass cell and into said reaction region; wherein the reagent ions react with the precursor ions within the reaction region to produce product ions.

16 Claims, 1 Drawing Sheet

(56) References Cited

U.S. PATENT DOCUMENTS

| | | |
|---|---|---|
| 8,071,938 B2 | 12/2011 | Guharay |
| 8,164,052 B2 | 4/2012 | Green et al. |
| 9,117,644 B2 | 8/2015 | Green et al. |
| 9,147,563 B2 | 9/2015 | Makarov |
| 9,255,906 B2 * | 2/2016 | Williams ............... G01N 27/62 |
| 9,484,194 B2 * | 11/2016 | Brown .................... H01J 49/00 |
| 2014/0291501 A1 | 10/2014 | Brown et al. |
| 2014/0346341 A1 | 11/2014 | Giles et al. |

\* cited by examiner

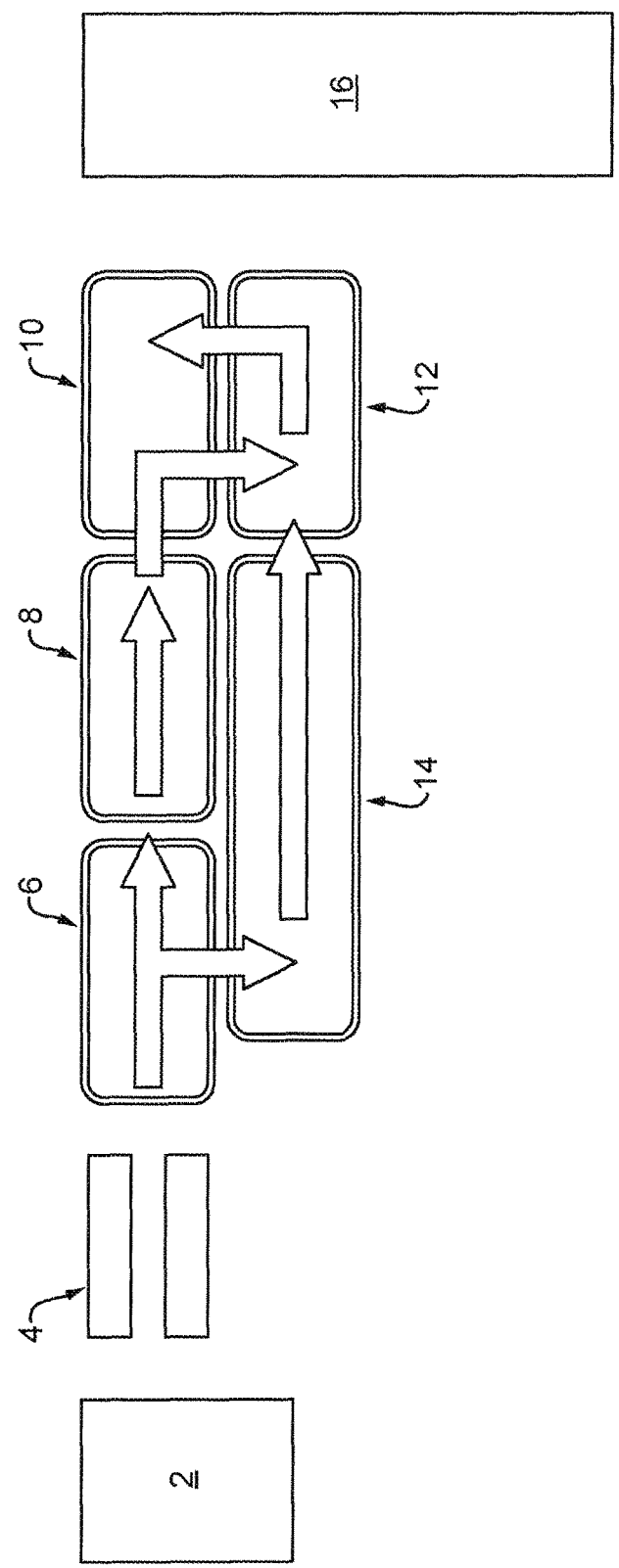

METHOD AND APPARATUS FOR REACTING IONS

CROSS-REFERENCE TO RELATED APPLICATION

This application is the National Stage of International Application No. PCT/GB2014/051768, filed 9 Jun. 2014 which claims priority from and the benefit of United Kingdom patent application No. 1310133.2 filed on 7 Jun. 2013 and European patent application No. 13170997.4 filed on 7 Jun. 2013. The entire contents of these applications are incorporated herein by reference.

BACKGROUND OF THE PRESENT INVENTION

It is known to dissociate precursor analyte ions by reacting the ions with reagent ions. For example, it is known to react reagent ions with precursor analyte ions so as to induce electron transfer dissociation (ETD) of the precursor ions.

GB 2441198 discloses a mass spectrometer comprising a plurality of ions storage banks. According to one arrangement disclosed therein, analyte ions from an ion source are reacted with ETD reagent ions from another ion source in an ion storage bank.

It is desired to provide and improved method of mass spectrometry and an improved mass spectrometer.

SUMMARY OF THE PRESENT INVENTION

The present invention provides a method of mass spectrometry that in a first mode comprises:
providing a source of precursor ions and reagent ions for reacting with said precursor ions;
providing a reaction region downstream of said source;
providing an ion mobility separator between said source and said reaction region;
providing a bypass cell between said source and said reaction region for guiding ions from said source to said reaction region without passing through said ion mobility separator;
guiding said precursor ions from said source, through said ion mobility separator so that said precursor ions separate according to their ion mobility and into said reaction region; and
guiding said reagent ions from said source, through said bypass cell and into said reaction region;
wherein the reagent ions react with the precursor ions within the reaction region to produce product ions.

The inventors have recognised that the present invention enables the reagent ions to be transferred from the ion source to the reaction region without having to pass into the relatively high pressure region of the ion mobility separator. This allows relatively labile reagent ions to be transmitted directly to the reaction region without fragmenting, which may otherwise occur if the ions were to enter into the high pressure ion mobility separator. Also, as the ion reactions occur in a reaction region downstream of the ion mobility separator, the potential barriers that may be required to transfer ions to the mass analyser detector, whilst maintaining the ion mobility separation of the ions, can be different and optimised so as to affect the ion reaction conditions. Furthermore, the ion-ion reaction is not limited by the time scales of the ion mobility separation and can be optimised separately.

As described in the Background of The Present Invention section above, it is known to react reagent ions with precursor ions. For example, GB 2441198 discloses a method in which analyte ions from one ion source are reacted with reagent ions from another ion source in an ion storage bank. However, GB 2441198 does not disclose passing the analyte ions through an ion mobility separator (IMS) prior to reacting the analyte ions with the reagent ions. The device is therefore unable to react the analyte ions and analyse the resulting product ions as a function of the ion mobility of the precursor analyte ions. As GB 2441198 does not disclose providing an IMS device, it also does not disclose providing a bypass cell for causing reagent ions to bypass such an IMS device. As the present invention provides the bypass cell claimed, this enables both the precursor analyte ions and the reagent ions to travel towards the IMS device along the same ion path, without the reagent ions passing through the IMS device arranged downstream of this ion path. The same ion guide may therefore be used to guide the precursor analyte ions and the reagent ions towards through part of the spectrometer.

Preferably, the reagent ions react with said precursor ions in the reaction region to cause electron transfer dissociation (ETD) of the precursor ions, and the product ions comprise fragment ions of the precursor ions. Alternatively, the reagent ions may react with the precursor ions in the reaction region to cause other types of reaction. For example, the reagent ions may react with the precursor ions in the reaction region to cause a proton transfer reaction, a charge inversion of said precursor ions, a Schiff base reaction, or a negative ion ETD reaction. Other types of reaction are also contemplated, such as reactions that form adduct ions.

The precursor ions are preferably guided through a high pressure gas as they pass through the ion mobility separator and the reagent ions are preferably guided through a low pressure gas as they pass through the bypass cell.

According to the present invention, the reagent ions and precursor ions are preferably guided through the same ion guide and the precursor ions are then directed through said ion mobility separator, whereas said reagent ions are directed through said bypass cell and into said reaction region.

Preferably, the reagent ions and precursor ions are guided along an axis through the same ion guide and an electric field is applied to said reagent ions and/or precursor ions whilst they are within said ion guide or at the exit of said ion guide such that the reagent ions are transmitted downstream into said bypass cell and said precursor ions are transmitted downstream into said ion mobility separator.

The reagent ions and precursor ions are preferably guided along an axis through the same ion guide and an electric field may be applied to the reagent ions whilst they are within the ion guide or at the exit of said ion guide so as to divert the reagent ions from said axis and into the bypass cell.

The axis may be substantially coaxial with a longitudinal axis through the ion mobility separator such that the precursor ions exiting said ion guide pass directly into the ion mobility separator. Alternatively, the reagent ions and precursor ions may be guided along an axis through the same ion guide and an electric field may be applied to the precursor ions whilst they are within said ion guide or at the exit of said ion guide so as to divert the precursor ions from said axis and into said ion mobility separator. It is therefore conceived that both the precursor ions and reagent ions may be diverted from the axis. Alternatively, only the precursor ions may be diverted from the axis and the non-diverted reagent ions may pass into the bypass cell, which is arranged with its entrance on said axis. Alternatively, only the reagent ions may be diverted from the axis and the non-diverted precursor ions may pass into the ion mobility separator, which is arranged with its entrance on said axis.

Preferably, the method comprises providing the reagent ions and precursor ions to the ion guide in a spatially separated manner; or spatially separating the reagent ions and precursor ions within the ion guide. A mass filter may be arranged between the ion guide and the source of precursor ions and reagent ions, and the mass filter may selectively transmit only the precursor ions during a first time period and selectively transmits only the reagent ions during a second time period such that the precursor ions and reagent ions are spatially separated when they are received in the ion guide. The mass filtering enables ions from the reagent ion source other than the reagent ions to be filtered out. This is advantageous as such other ions may cause charge stripping, rather than causing the desired reaction, such as an ETD reaction. The mass filter may repeat this cycle between said first and second time periods a plurality of times such that precursor ions and reagent ions are alternately received at the ion guide. The mass filter is preferably a multipole rod set, such as a quadrupole rod set, to which RF and DC voltages may be applied so as to selectively transmit the desired ions and reject other ions. An alternative arrangement is contemplated wherein the above-described mass filter is said ion guide, rather than providing the mass filter in addition to the ion guide.

The reagent ions are preferably maintained spatially separated from the precursor ions within the ion guide by one or more potential well or potential barrier arranged between the precursor ions and the reagent ions. The one or more potential well or barrier may be conveyed along the ion guide so as to move said reagent ions and precursor ions from an entrance of the ion guide towards an exit of the ion guide.

The method preferably comprises applying an electric field to the reagent ions that are spatially separated from the precursor ions so as to divert the reagent ions into the bypass cell; and/or applying an electric field to the precursor ions that are spatially separated from the reagent ions so as to divert the precursor ions into the ion mobility separator.

One or more potential barriers or potential wells may be conveyed along the axial length of the ion mobility separator so as to drive the precursor ions through the ion mobility separator.

Ions exit the ion mobility separator separated according to their ion mobilities, and precursor ions having ion mobilities of interest may be selectively introduced into the reaction region and reacted with the reagent ions within the reaction region. Other precursor ions may not be transmitted to the reaction region or not reacted with reagent ions in the reaction region.

One or more potential barrier or potential well may be conveyed along the axial length of the bypass cell so as to drive the reagent ions through the bypass cell and into the reaction region. The one or more potential barrier or potential well may inject reagent ions into the reaction region in packets, and the injection of said packets may be synchronised with the injection of precursor ions of interest into the reaction region from the ion mobility separator. The reagent ions could alternatively be gated in another way so as to periodically enter the reaction region.

One or more potential barrier or potential well may be conveyed along the axial length of the ion mobility separator so as to drive the precursor ions through the ion mobility separator and into the reaction region. The one or more potential barrier or potential well may inject precursor ions into the reaction region in packets, and the injection of the packets of precursor ions may be synchronised with the injection of reagent ions into the reaction region.

The precursor ions and reagent ions react in the reaction region to form product ions and one or more potential barriers or potential wells may be conveyed along the axial length of the reaction region so as to drive the product ions towards an exit of the reaction region. The motion of the one or more potential barriers or wells through the reaction region may be synchronised with the injection of packets of precursor ions from the ion mobility separator (and optionally with the injection of packets of reagent ions from the bypass cell) such that a first packet of precursor ions reacts with reagent ions in the reaction region and the product ions thereof are conveyed along the reaction region by a first of said one or more potential barriers or wells of the reaction region, and a second packet of precursor ions that is injected into the reaction region after said first packet of precursor ions reacts with reagent ions in the reaction region and the product ions thereof are conveyed along the reaction region by a second, subsequent one of said one or more potential barriers or wells of the reaction region.

A mass analyser is provided downstream of the reaction region for mass analysing ions released from the reaction region. The mass analyser is preferably a time of flight mass analyser, more preferably an orthogonal acceleration time of flight mass analyser. The product ions released from the reaction region may be released in packets and the release of these packets may be synchronised with the pulsing of an acceleration electrode in the time of flight mass analyser such that each packet of ions released from the reaction region is pulsed into the time of flight region of the mass analyser by the acceleration electrode. The product ions may be released from the reaction region in packets due to the one or more potential barriers or wells that are conveyed along the reaction region.

The method may further comprise providing a plurality of different reaction regions downstream of the ion mobility separator and bypass cell, wherein reagent ions are supplied to the reaction regions from the bypass cell, and wherein precursor ions of different ion mobility exiting the ion mobility separator are directed into different ones of the reaction regions so as to react with the precursor ions to generate product ions. This is advantageous in terms of sensitivity given that several species can be reacted separately in parallel.

Said source of precursor ions and reagent ions may comprise a precursor ion source and a separate reagent ion source.

Said source(s) of ions may generate said ions or may be an ion trap or other source that releases ions that have been generated elsewhere.

The precursor ions themselves may be product or fragment ions, formed by reacting or fragmenting ions, e.g. by CID, ETD, ECD, SID, photo-fragmentation.

The method may comprise performing a second mode of operation wherein precursor ions are not guided through the ion mobility separator but are guided through the bypass cell and are then mass analysed in a mass analyser without having reacted with said reagent ions. The mass analyser may determine that precursor ions of interest are being generated by the source of precursor ions and, in response thereto, the method may be controlled to perform the first mode of operation such that the precursor ions of interest are guided to the ion mobility separator and (optionally) subsequently reacted with reagent ions in the reaction region to form said product ions. The product ions may then be mass analysed. The product ions generated from the precursor ions of interest may then be correlated to their precursor ions. For example, the product ions may be correlated to their precursor ions by the timings at which the product and precursor ions are detected by the mass analyser The present invention also provides a mass spectrometer comprising:

a source of precursor ions and reagent ions for reacting with said precursor ions;

a reaction region downstream of said source;

an ion mobility separator arranged between said source and said reaction region; and a bypass cell arranged between said source and said reaction region for guiding ions from said source to said reaction region without passing through said ion mobility separator;

wherein the mass spectrometer is arranged and configured to guide said precursor ions from said source, through said ion mobility separator and into said reaction region; and to guide said reagent ions from said source, through said bypass cell and into said reaction region for reacting the reagent ions with the precursor ions within the reaction region to produce product ions.

The mass spectrometer may be arranged and configured to perform any one or any combination of the methods described herein.

The mass spectrometer may comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may comprise an electrostatic ion trap or mass analyser that employs inductive detection and time domain signal processing that converts time domain signals to mass to charge ratio domain signals or spectra. Said signal processing may include, but is not limited to, Fourier Transform, probabilistic analysis, filter diagonalisation, forward fitting or least squares fitting.

The mass spectrometer may either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The mass spectrometer may comprise a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

According to an embodiment analyte ions may be subjected to Electron Transfer Dissociation ("ETD") fragmentation in an Electron Transfer Dissociation fragmentation device. Analyte ions are preferably caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions preferably comprise peptides, polypeptides, proteins or biomolecules.

In order to effect Electron Transfer Dissociation, optionally: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene reagent ions.

BRIEF DESCRIPTION OF THE DRAWING

An embodiment of the present invention will now be described, by way of example only, and with reference to FIG. 1, which shows a schematic of a mass spectrometer according to a preferred embodiment.

DETAILED DESCRIPTION OF PREFERRED EMBODIMENTS

A preferred embodiment of the present invention will now be described with reference to FIG. 1. FIG. 1 shows a schematic of a mass spectrometer according to a preferred embodiment of the present invention. The mass spectrometer comprises an ion source 2, a quadrupole rod set 4, an ion guide 6, an ion mobility separator (IMS) 8, a transfer cell 10, a reaction cell 12, a bypass cell 14 and a time of flight (TOF) mass analyser 16. The mass spectrometer is configured to perform electron transfer dissociation (ETD) reactions on precursor analyte ions that have been separated according to their ion mobility.

Precursor analyte ions and reagent ions are generated in the ion source 2. The precursor ions and reagent ions are directed downstream to the quadrupole rod set 4. The voltages that are applied to the quadrupole rod 4 select which mass to charge ratios are transmitted by the rod set 4. Initially, the voltages applied to the quadrupole rod set 4 are such that only the reagent ions are transmitted. The reagent ions then continue downstream to the ion guide 6. The voltages applied to the quadrupole rod set 4 are then altered such that the rod set 4 transmits precursor analyte ions and rejects the reagent ions. These precursor ions are transmitted downstream to the ion guide 6. The quadrupole rod set 4 may be repeatedly alternated so as to alternately transmit reagent ions and precursor analyte ions to the ion guide 6.

The reagent ions and precursor ions may be maintained separate in the ion guide 6 by applying a potential barrier between the packet of reagent ions and the packet of precursor ions. The potential barrier is preferably moved along the axial length of the ion guide 6 from the entrance towards the exit so as to move the reagent ions through the ion guide 6. Another potential barrier may be applied behind the precursor ions and that potential barrier may be moved along the ion guide 6 so as to urge the precursor ions towards the exit of the ion guide 6. The quadrupole rod set 4 may then be controlled so as to transmit another packet of reagent ions or a packet of precursor analyte ions of a different mass to charge ratio to the previously transmitted precursor ions. This packet of reagent ions or precursor ions may then be received in the ion guide 6 behind the first packet of precursor ions and will remain separated from those ions by the potential barrier behind the first packet of precursor ions. Potential barriers may be periodically generated at the entrance of the ion guide 6 and each barrier conveyed towards the exit of the ion guide 6. This enable packets of ions to be continuously received from the quadrupole rod set 4, wherein each packet of ions is received behind the latest potential barrier to be generated and wherein each packet of ions becomes trapped between adjacent potential barriers and conveyed towards the exit of the ion guide 6.

The ion guide 6 is controlled so as to transmit precursor analyte ions into the IMS device 8 and to transmit reagent ions into the bypass cell 14. This may be achieved by controlling the voltages applied to the ion guide 6. As described above, reagent ions are transmitted through the ion guide 6 by being conveyed between adjacent potential barriers. When these reagent ions are at the desired axial location in the ion guide 6, a voltage is applied to an electrode in the ion guide and/or an electrode in the bypass cell 14 so as to cause the reagent ions to be ejected orthogonally from their direction of travel and to pass into the bypass cell 14. The bypass cell 14 is maintained at a relatively low pressure and preferably contains an inert gas (e.g. helium gas at $10^{-2}$ mBar). The reagent ions continue to travel along the length of the bypass cell 14 and then pass into the reaction cell 12. The reagent ions may be urged along the bypass cell 14 and into the reaction cell 12 by one or more potential barriers that are conveyed along the bypass cell 14 from the entrance region to the exit region. The reagent ions then reside in the reaction cell 12 for reacting with any precursor analyte ions that may be introduced into the reaction cell 12.

The precursor ions in the ion guide 6 are not ejected into the bypass cell 14, but continue to the end of the ion guide 6, at which point the potential barrier leading the packet of precursor ions drops and the precursor ions are released into the IMS device 8. The IMS device 8 may be at a relatively high pressure, as compared to the bypass cell 14, and the precursor ions must be driven through the gas in the IMS device 8. This may be achieved by conveying a potential barrier along the axial length of the IMS device 8 from the entrance to the exit. Potential barriers are preferably periodically conveyed along the IMS device 8 so as to sweep the precursor ions through the IMS device 8. As the ions are swept through the gas in the IMS device 8 they interact with the gas molecules and become separated according to their mobility through the gas. Accordingly, ions of high ion mobility will pass through the gas and exit the IMS device 8 relatively quickly, whereas ions of low ion mobility will pass through the gas and exit the IMS device 8 relatively slowly. It is desirable to subject precursor analyte ions of interest to ETD reactions with the reagent ions. As described above, the ion mobilities of the precursor ions are related to their transit times through the IMS device 8. Accordingly, precursor ions having ions mobilities of interest may be selected according to the time at which they exit the IMS device 8. The precursor ions exit the IMS device 8 and enter the transfer cell 10. Precursor ions of interest are then passed from the transfer cell 10 into the reaction cell 12. This may be achieved by applying a voltage to the transfer cell 10 and/or reaction cell 12.

The precursor ions that enter the reaction cell 12 interact with the reagent ions present therein and dissociate as a result of ETD reactions into product ions. The resulting product ions may be directed along the reaction cell 12 and then directed back into the transfer cell 10 by applying a voltage to the reaction cell 12 and/or transfer cell 10. The product ions may then be directed into the TOF mass analyser 16 for mass analysis.

The preferred embodiment allows precursor ions to be passed through an IMS device 8, whilst allowing the reagent ions to be bypass the IMS device 8. This enables the reagent ions to be passed from the ion source 2 to the reaction region 12 without being subjected to the high pressure region of the IMS device 8, which may otherwise result in the undesirable fragmentation of the reagent ions.

Although the present invention has been described with reference to preferred embodiments, it will be understood by those skilled in the art that various changes in form and detail may be made without departing from the scope of the invention as set forth in the accompanying claims.

For example, instead of a single reaction cell 12, a plurality of different reaction cells may be arranged downstream of the IMS device 8 and bypass cell 14. Reagent ions may be supplied to the reaction cells from the bypass cell 14 and precursor ions of different ion mobility exiting the IMS device 8 may be directed into different ones of the reaction cells so as to react with the precursor ions to generate product ions. This is advantageous in terms of sensitivity as several species of precursor ions can be reacted separately in parallel.

It is contemplated that standard drift tube technology could be applied for the IMS device 8.

Although ETD fragmentation has been described, it is also contemplated that photo-fragmentation or excitation or other ion-molecule or ion-ion reactions may be induced in the reaction cell(s) 12. For example, collisional induced dissociation (CID) may be induced in the reaction cell(s) 12. This may be useful, for example, in order to assist the precursor ions in fully dissociating after the ETD reactions (or other reactions).

Although precursor analyte ions have been described as being transmitted through the ion guide 6 and IMS device 8 to the reaction cell 12, it is contemplated that the precursor ions may be reacted or fragmented to produce product or fragment ions prior to reaching the reaction cell 12 and that these product or fragment ions may then be subjected to the above-described fragmentation or reactions in the reaction cell 12. The precursor ions may be fragmented or reacted via any process, such as a CID, ETD, ECD, SID (Surface Induced Dissociation) or photo-fragmentation technique. For example, the precursor ions may be trapped in the ion guide 6 and subjected to fragmentation or reactions. The resulting product or fragment ions may then be separated in the IMS device 8 for subsequent ETD (ion-ion) reactions in the reaction cell 12.

It is contemplated that the quadrupole 4 may be used to mass select ions eluting from an IMS-Q (TOF) geometry, rather that filtering ions directly from the ion source 2.

It is also contemplated that in another additional mode of operation the precursor ions may bypass the IMS device 8 and the be directed to the TOF mass analyser 16 without being separated according to their ion mobility. The TOF detector may then be used to determine which ions are subjected to analysis in the IMS device 8 (e.g. to perform a DDA, HDMS^e technique).

The ion guide 6 and the bypass cell 14 may have a StepWave configuration for transmitting the reagent ions from the ion guide 6 to the bypass cell 14. The transfer cell 10 and reaction cell 12 may have a StepWave configuration for transmitting the precursor ions into the reaction cell 12 and for transferring precursor ions or product ions from the reaction cell 12 to the transfer cell 10. As an alternative, "Entwistle sandwich plate" guides may be used to divert ion beams rather than a StepWave device.

It is also contemplated that the reaction cell 12 could be a quadrupole or linear ion guide having mass selective functionality.

The invention claimed is:

1. A method of mass spectrometry having a first mode comprising:
   providing a source of precursor ions and reagent ions for reacting with said precursor ions;
   providing a reaction region downstream of said source;
   providing an ion mobility separator between said source and said reaction region;
   providing a bypass cell between said source and said reaction region for guiding ions from said source to said reaction region without the ions passing through said ion mobility separator;
   guiding said precursor ions from said source, through said ion mobility separator so that said precursor ions separate according to their ion mobility and into said reaction region; and
   guiding said reagent ions from said source, through said bypass cell and into said reaction region;
   wherein the reagent ions react with the precursor ions within the reaction region to produce product ions.

2. The method of claim 1, wherein said reagent ions react with said precursor ions in said reaction region to cause electron transfer dissociation of the precursor ions, and wherein the product ions comprise fragment ions of the precursor ions; or wherein said reagent ions react with said precursor ions in said reaction region to cause a proton transfer reaction, a charge inversion of said precursor ions, a Schiff base reaction or a negative ion electron transfer dissociation reaction.

3. The method of claim 1, wherein the precursor ions are guided through a gas at a first pressure as they pass through the ion mobility separator, and the reagent ions are guided through a gas at a second, lower pressure as they pass through the bypass cell.

4. The method of claim 1, wherein the reagent ions and precursor ions are guided through the same ion guide, and wherein the precursor ions are subsequently directed through said ion mobility separator, whereas said reagent ions are subsequently directed through said bypass cell.

5. The method of claim 1, wherein said reagent ions and precursor ions are guided along an axis through the same ion guide and an electric field is applied to said reagent ions and/or precursor ions whilst they are within said ion guide or at the exit of said ion guide such that said reagent ions are transmitted downstream into said bypass cell and said precursor ions are transmitted downstream into said ion mobility separator.

6. The method of claim 5, wherein the electric field is applied to said reagent ions whilst they are within said ion guide or at the exit of said ion guide so as to divert the reagent ions from said axis and into said bypass cell.

7. The method of claim 5, comprising providing said reagent ions and precursor ions to said ion guide in a spatially separated manner; or spatially separating said reagent ions and precursor ions within said ion guide prior to the application of the electric field.

8. The method of claim 7, wherein a mass filter is arranged between said ion guide and said source of precursor ions and reagent ions, and wherein said mass filter selectively transmits only said precursor ions during a first time period and selectively transmits only said reagent ions during a second time period such that the precursor ions and reagent ions are spatially separated when they are received in the ion guide.

9. The method of claim 7, wherein said reagent ions are maintained spatially separated from said precursor ions within said ion guide by one or more potential well or potential barrier arranged between said precursor ions and said reagent ions.

10. The method of claim 7, comprising applying an electric field to the reagent ions that are spatially separated from the precursor ions so as to divert the reagent ions into said bypass cell; and/or applying an electric field to the precursor ions that are spatially separated from the reagent ions so as to divert said precursor ions into said ion mobility separator.

11. The method of claim 1, wherein two or more potential barriers or wells are conveyed along the reaction region and precursor ions are injected into said reaction region from said ion mobility separator as ion packets, and wherein the motion of the two or more potential barriers or wells is synchronised with the injection of the packets of precursor ions such that a first packet of precursor ions reacts with reagent ions in the reaction region and the product ions thereof are conveyed along the reaction region by a first of said potential barriers or wells, and a second packet of precursor ions that is injected into the reaction region reacts with reagent ions in the reaction region and the product ions thereof are conveyed along the reaction region by a second, subsequent one of said potential barriers or wells.

12. The method of claim 1, further comprising performing a second mode of operation wherein precursor ions are not guided through the ion mobility separator but are guided through the bypass cell and are then mass analysed in a mass analyser without having reacted with said reagent ions.

13. The method of claim 12, wherein in the second mode the mass analyser determines that precursor ions of interest are being generated by the source of precursor ions and in response thereto controls the method to perform the first mode of operation such that the precursor ions of interest are guided to the ion mobility separator and subsequently reacted with reagent ions in the reaction region to form said product ions.

14. The method of claim 13, wherein the product ions are mass analysed and these product ions are correlated to their precursor ions detected in the second mode, optionally based on the timings at which the product and precursor ions are detected by the mass analyser.

15. A mass spectrometer comprising:
   a source of precursor ions and reagent ions for reacting with said precursor ions;
   a reaction region downstream of said source;
   an ion mobility separator arranged between said source and said reaction region; and
   a bypass cell arranged between said source and said reaction region for guiding ions from said source to said reaction region without passing through said ion mobility separator;
   wherein the mass spectrometer is arranged and configured to guide said precursor ions from said source, through said ion mobility separator and into said reaction region; and to guide said reagent ions from said source, through said bypass cell and into said reaction region for reacting the reagent ions with the precursor ions within the reaction region to produce product ions.

16. The mass spectrometer of claim 15, wherein the spectrometer is arranged and configured with control means.

* * * * *